(12) United States Patent
Tierney et al.

(10) Patent No.: US 12,357,324 B2
(45) Date of Patent: Jul. 15, 2025

(54) INTRAOSSEOUS ACCESS DEVICE AND LOCATOR ASSEMBLY

(71) Applicant: TELEFLEX LIFE SCIENCES LIMITED, Valletta (MT)

(72) Inventors: Morgan Tierney, Ferbane (IE); Aleksejus Fominas, Athlone (IE); Wade Kevin Trexler, Coopersburg, PA (US); Kurt Donald Heinly, Wernersville, PA (US); David Troy Rowe, Fleetwood, PA (US); Stephan M. Huhn, Manheim, PA (US)

(73) Assignee: Teleflex Life Sciences II LLC, Wilmington, DE (US)

( * ) Notice: Subject to any disclaimer, the term of this patent is extended or adjusted under 35 U.S.C. 154(b) by 748 days.

(21) Appl. No.: 17/555,221

(22) Filed: Dec. 17, 2021

(65) Prior Publication Data

US 2022/0110642 A1    Apr. 14, 2022

Related U.S. Application Data

(63) Continuation of application No. PCT/IB2020/055197, filed on Jun. 2, 2020.
(Continued)

(51) Int. Cl.
*A61B 17/34* (2006.01)
*A61B 17/16* (2006.01)
*A61B 17/00* (2006.01)

(52) U.S. Cl.
CPC ...... *A61B 17/1691* (2013.01); *A61B 17/3472* (2013.01); *A61B 17/3496* (2013.01); *A61B 2017/00424* (2013.01)

(58) Field of Classification Search
CPC ..... A61B 17/16; A61B 17/34; A61B 17/3417; A61B 17/1691; A61B 17/3472; A61B 2017/349; A61B 2017/00247
See application file for complete search history.

(56) References Cited

U.S. PATENT DOCUMENTS

| 2,426,535 | A | * | 8/1947 | Turkel | A61M 5/158 |
| | | | | | 600/567 |
| 3,815,605 | A | * | 6/1974 | Schmidt | A61M 5/00 |
| | | | | | 606/182 |

(Continued)

FOREIGN PATENT DOCUMENTS

| CN | 107684451 A | 2/2018 |
| WO | 2013009901 A2 | 1/2013 |
| WO | 2019215705 A1 | 11/2019 |

OTHER PUBLICATIONS

International Search Report for International application No. PCT/IB2020/055197, mailed Jul. 24, 2020.

*Primary Examiner* — Vi X Nguyen
(74) *Attorney, Agent, or Firm* — BakerHostetler

(57) ABSTRACT

An intraosseous access device for accessing an intraosseous space of a patient includes a manual driver and a sternal locator. The handle is connected to an inner penetrator hub, and an inner penetrator extends from the inner penetrator hub. An outer penetrator hub is releasably engaged to the inner penetrator hub. A protective cover is slidably coupled to the handle. The protective cover is operable to move from an extended position where the inner penetrator is covered, to a retracted position where the inner penetrator is exposed. The sternal locator includes a base; a collar extending from a first surface of the base for securing the intraosseous access device to restrict longitudinal separation of the intraosseous access device from the locator. The locator may be removed (Continued)

from the patient while the outer penetrator remains inserted in an intraosseous space of the patient.

11 Claims, 11 Drawing Sheets

Related U.S. Application Data

(60) Provisional application No. 62/865,170, filed on Jun. 22, 2019.

(56) References Cited

U.S. PATENT DOCUMENTS

| 4,787,893 A * | 11/1988 | Villette ........... A61C 19/08 |
| | | 604/188 |
| 2010/0312246 A1 | 12/2010 | Browne |
| 2013/0041345 A1 | 2/2013 | Kilcoin et al. |

* cited by examiner

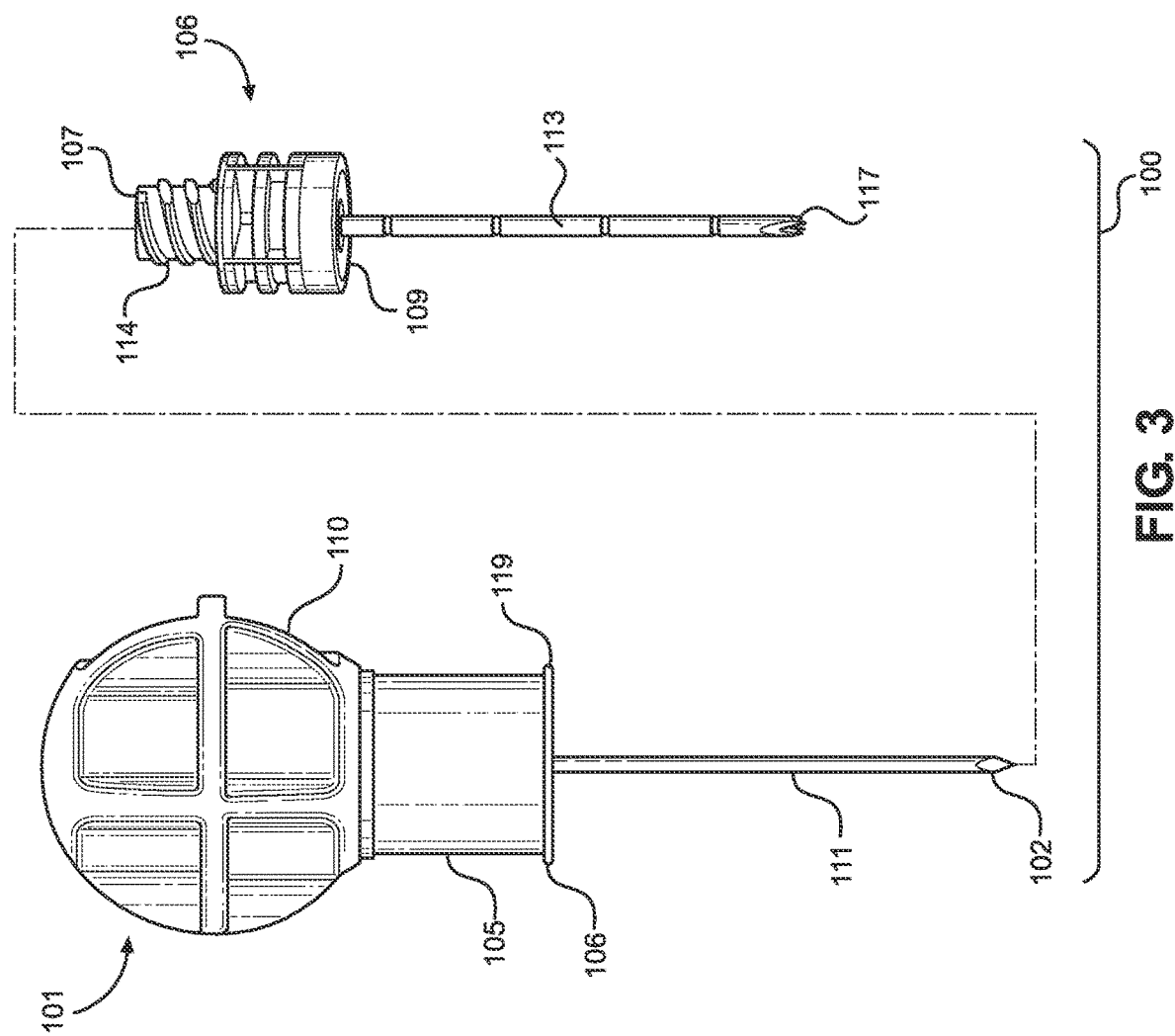

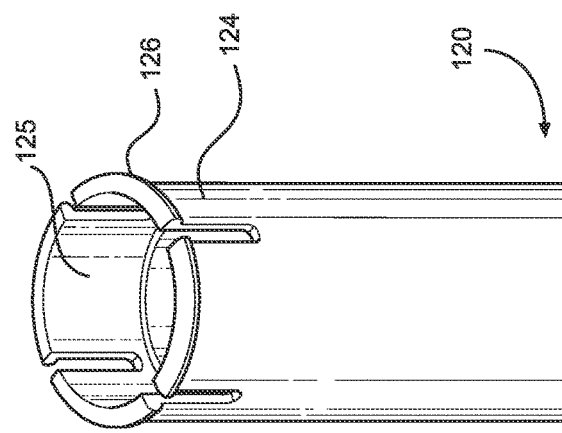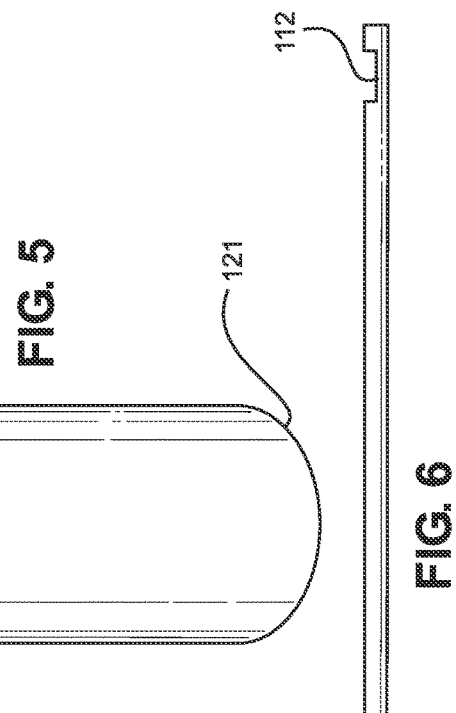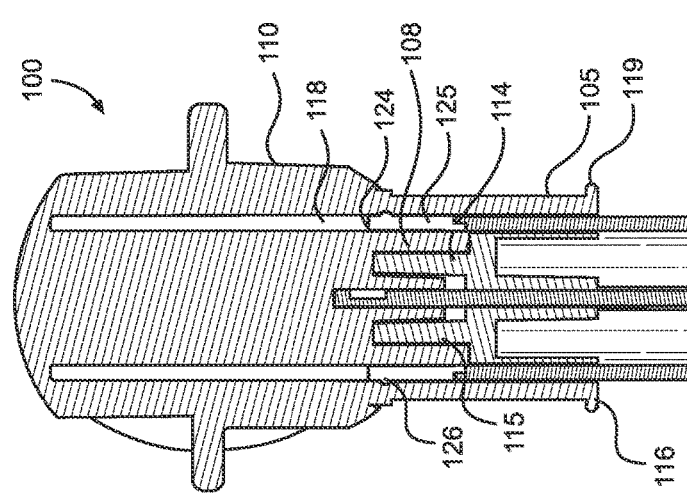

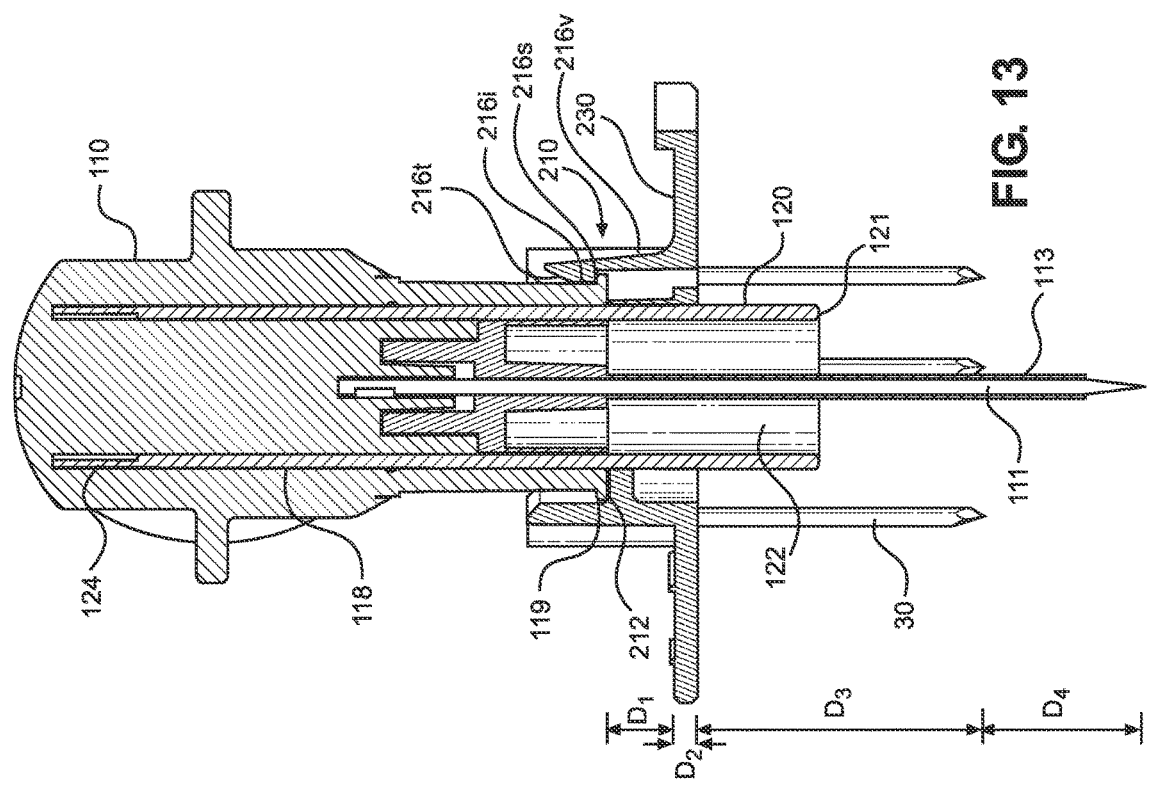
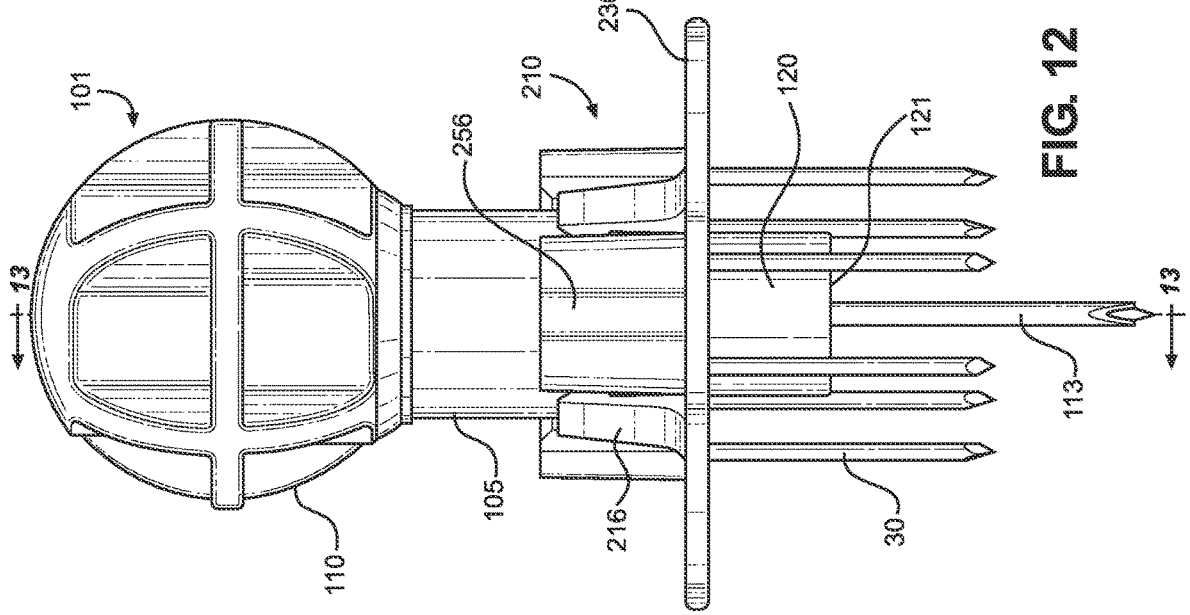

INTRAOSSEOUS ACCESS DEVICE AND LOCATOR ASSEMBLY

CROSS-REFERENCE TO RELATED APPLICATIONS

The present application is a Continuation of International Application PCT/IB2020/055197, filed Jun. 2, 2020, which claims the benefit of priority to U.S. Provisional Patent Application No. 62/865,170, filed Jun. 22, 2019, the contents of which are incorporated herein in their entirety.

TECHNICAL FIELD

The present disclosure generally relates to a medical apparatus for locating and accessing an intraosseous space of a patient. More specifically, the present disclosure relates to an intraosseous access device and locator assembly for placement of a conduit into the intraosseous space within a bone of a patient.

BACKGROUND

Many life-threatening emergencies, including shock, trauma, cardiac arrest, drug overdoses, diabetic ketoacidosis, arrhythmias, burns, and status epilepticus, just to name a few, often unnecessarily result in death because intravenous (IV) access cannot be achieved in a timely manner. An essential element for treating many life threatening emergencies is the rapid establishment of an IV line in order to administer drugs and fluids directly into a patient's vascular system. Whether in an ambulance by paramedics, in an emergency room by emergency specialists or on a battlefield by an Army medic, the goal is the same—quickly start an IV in order to administer lifesaving drugs and fluids. To a large degree, ability to successfully treat most critical emergencies is dependent on the skill and luck of an operator in accomplishing vascular access. While relatively easy to start an IV on some patients, doctors, nurses and paramedics may nevertheless experience difficulty establishing IV access in some patients. The success rate on the battlefield may be much lower, in which wounded soldiers are often probed repeatedly with sharp needles in an attempt to quickly establish IV access.

In the case of patients with chronic disease or the elderly, availability of easily accessible veins may be depleted. Other patients may have no available IV sites due to anatomical scarcity of peripheral veins, obesity, extreme dehydration or previous IV drug use. For such patients, finding a suitable site for administering lifesaving therapy often becomes a monumental and frustrating task. As a result, patients with life threatening emergencies may die when access to the vascular system with lifesaving IV therapy is delayed or simply not possible.

There are various circumstances under which it is desirable to introduce drugs or other liquids into the marrow of a subject's bone. For example, in cases where a subject has suffered from serious trauma or cardiac arrest it may not be practical to deliver liquids by way of intravenous (IV) infusions. Intraosseous infusion may also be useful for delivering fluids to newborns and small children in which suitable blood vessels are difficult to access. Intraosseous infusion may be used to deliver fluids into a subject's sternum, humerus, femur, tibia, or other bone. Intraosseous infusion has the advantage that, with appropriate technology, a pathway for intraosseous infusion can be established very rapidly. This can save lives in critical situations. Portals in bone may also be applied to withdraw or aspirate fluid from within the bone.

The intraosseous (TO) space provides a direct conduit to a patient's vascular system and provides an attractive alternate route to administer IV drugs and fluids. Drugs administered intraosseously enter a patient's blood circulation system rapidly, thus bone marrow may function as a large non-collapsible vein.

Proper placement of an intraosseous needle in the bone is critical. If a user attempts to insert the needle in the wrong place, the bone might be too thick and therefore difficult for the needle to penetrate. Alternatively, the bone might be too thin, in which case the needle could completely penetrate the anterior and posterior sides of the bone, thus missing the intraosseous region entirely. Also, placing the needle at an angle that is not substantially perpendicular to the surface of the bone may lead to the needle breaking, or other complications. Furthermore, certain powered drivers are unable to successfully penetrate bone when their respective power source is depleted. Additionally, the sharp penetrator tips of conventional driver assemblies can be dangerous if they are accidentally mishandled by a user prior to a planned insertion procedure. For instance, without adequate sharps protection, the user is susceptible to accidentally poking himself or another individual with the penetrator.

Therefore, a need exists for an intraosseous access device and locator assembly operable to locate a suitable insertion site and provide a quick and easy conduit to an intraosseous space within a bone of a patient.

SUMMARY

The foregoing needs are met by implementations of an apparatus for accessing an intraosseous space within a bone of a patient according to the present disclosure. According to one aspect of the disclosure, the apparatus comprises a penetrator assembly having a sharp penetrating end configured to penetrate the bone and associated bone marrow; a manual driver coupled to the penetrator assembly, the manual driver including a handle operable to manually drive the penetrator assembly into the bone and associated bone marrow; and a protective shield having a distal end and a proximal end, the protective shield slidably coupled to the handle and defining a longitudinal hollow passageway extending between the distal end and the proximal end; where the protective shield is operable to move between an extended position in which the sharp penetrating end of the penetrator assembly is disposed within the longitudinal hollow passageway of the protective shield to provide sharps protection, and a retracted position in which the sharp penetrating end of the penetrator assembly is disposed outside the longitudinal hollow passageway of the protective shield to permit penetration of the penetrator assembly into the intraosseous space.

According to another aspect of the disclosure, the distal end of the protective shield defines an opening sized to receive the penetrator assembly.

According to another aspect of the disclosure, the distal end of the protective shield includes a blunt surface operable to contact a patient's skin without cutting the skin.

According to another aspect of the disclosure, the protective shield is removably coupled to the handle.

According to another aspect of the disclosure, the driver further comprises an internal recess configured to slidably receive the protective shield.

According to another aspect of the disclosure, the proximal end of the protective shield includes a resilient finger.

According to another aspect of the disclosure, at least two spaced-apart resilient fingers are disposed along a circumference of the proximal end of the protective shield.

According to another aspect of the disclosure, each resilient finger includes an outwardly protruding ridge configured to provide a friction fit within the internal recess of the driver to maintain the protective shield in a desired position.

According to another aspect of the disclosure, the internal recess has a shape corresponding to a shape of the protective shield.

According to another aspect of the disclosure, the protective shield is generally cylindrical, and the internal recess is correspondingly annular.

According to another aspect of the disclosure, the penetrator assembly further comprises an outer penetrator defining a longitudinal hollow bore, and an inner penetrator slidably receivable within the hollow bore of the outer penetrator.

According to another aspect of the disclosure, the inner penetrator comprises a rigid stylet, and the outer penetrator comprises a flexible cannula.

According to another aspect of the disclosure, an outer penetrator hub is coupled to the outer penetrator, the outer penetrator hub being removably attachable to the manual driver.

According to another aspect of the disclosure, the outer penetrator hub comprises a proximal end including an external threaded surface configured to releasably engage a corresponding internal threaded surface of the manual driver.

According to another aspect of the disclosure, the manual driver further comprises an inner penetrator hub coupled to the inner penetrator.

According to another aspect of the disclosure, a skirt extends from the handle.

According to another aspect of the disclosure, the skirt comprises a distal end having an outwardly extending flange.

According to another aspect of the disclosure, the handle has an ergonomic grip shape suitable for grasping during manual insertion of the penetrator assembly into the bone and associated bone marrow; and wherein the handle is configured to allow manual force to be applied and at the same time permit rotation of the handle.

According to another aspect of the disclosure, the apparatus further comprises a sternal locator including: a base having a first surface, a second surface, and a through-hole extending through the base; and a collar extending from the first surface of the base, the collar configured to secure the manual driver to restrict longitudinal separation of the manual driver from the locator, the collar surrounding the through-hole and defining a passageway configured to receive the protective shield for guiding insertion of the penetrator assembly into the intraosseous space without restricting movement of the protective shield between its extended and retracted positions during an insertion procedure.

According to another aspect of the disclosure, the collar further comprises a collar contact surface configured to contact a distal end of a skirt extending from the manual driver to impede further insertion of the penetrator assembly into the intraosseous space.

According to another aspect of the disclosure, the locator further comprises a bone probe extending from a second surface of the base.

According to another aspect of the disclosure, the locator is operable to be removed from the patient while an outer penetrator of the penetrator assembly remains inserted in the intraosseous space of the patient.

According to another aspect of the disclosure, a method of accessing an intraosseous space within a sternum of a patient comprises providing an intraosseous access device including a penetrator assembly having a sharp penetrating end, a manual driver coupled to the penetrator assembly, and a protective shield slidably coupled to the driver and defining a longitudinal hollow passageway; providing a sternal locator including a base having a first surface and a second surface, a through-hole extending through the first and second surfaces of the base, a collar extending from the first surface of the base and surrounding the through-hole, and a bone probe extending from the second surface of the base; positioning the through-hole of the sternal locator over the sternum; inserting the bone probe into the patient until the bone probe contacts the sternum; introducing the protective shield of the intraosseous access device into the through-hole in the base of the locator for guiding insertion of the penetrator assembly into the sternum; and manually inserting the penetrator assembly into the intraosseous space within the sternum.

According to another aspect of the disclosure, manually inserting the penetrator assembly comprises grasping an ergonomically-shaped handle of the driver and manually applying force toward the insertion site and at the same time manually turning the handle.

According to another aspect of the disclosure, a distal end of the protective shield contacts the patient's skin during insertion of the penetrator assembly into the intraosseous space.

According to another aspect of the disclosure, the protective shield is movable from an extended position to a retracted position during insertion of the penetrator assembly into the intraosseous space.

According to another aspect of the disclosure, the penetrator assembly comprises an inner penetrator and an outer penetrator, the inner penetrator slidably disposed within a longitudinal hollow bore of the outer penetrator.

According to another aspect of the disclosure, the inner penetrator is withdrawn from the outer penetrator while the outer penetrator remains inserted within the intraosseous space.

According to another aspect of the disclosure, the locator is withdrawn from the patient while the outer penetrator remains inserted within the intraosseous space.

According to another aspect of the disclosure, the protective shield is moved back to the extended position from the retracted position during withdrawal of the inner penetrator from the intraosseous space to provide sharps protection for the inner penetrator.

There has thus been outlined certain aspects of the disclosure in order that the detailed description thereof may be better understood, and in order that the present contribution to the art may be better appreciated. There are additional implementations of the disclosure that will be described below and which form the subject matter of the claims appended hereto.

In this respect, before explaining at least one aspect of the intraosseous access device in detail, it is to be understood that the apparatus is not limited in its application to the details of construction and to the arrangements of the components set forth in the following description or illustrated in the drawings. The intraosseous access device is capable of aspects in addition to those described, and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the intraosseous access device. It is important, therefore, that the claims be regarded as including such equivalent constructions insofar as they do not depart from the spirit and scope of the disclosure.

BRIEF DESCRIPTION OF THE DRAWINGS

In order that the disclosure may be readily understood, aspects of the intraosseous (IO) access device are illustrated by way of examples in the accompanying drawings, in which like parts are referred to with like reference numerals throughout.

FIG. 3 illustrates a partially exploded side view of the intraosseous access device according to the present disclosure.

FIG. 4D illustrates a cross-sectional side view of the intraosseous access device of FIG. 4A.

FIG. 5 illustrates a perspective view of a shield of the intraosseous access device of the present disclosure.

FIG. 6 illustrates a side view of an inner penetrator of the intraosseous access device of the present disclosure.

FIG. 12 illustrates a side elevation view of the intraosseous access device and locator assembly in accordance with the present disclosure.

FIG. 13 illustrates a cross-section view of the intraosseous access device and locator assembly taken along line 13-13 in FIG. 12.

DETAILED DESCRIPTION

The present disclosure provides an intraosseous access device and locator assembly for locating a suitable insertion site and penetrating the underlying bone, such as a human patient's sternum, and quickly and easily providing a conduit to an intraosseous space within the bone for associated medical procedures, including delivery of fluid and medication, aspiration, and biopsy of bone marrow, among others.

Figure 1:
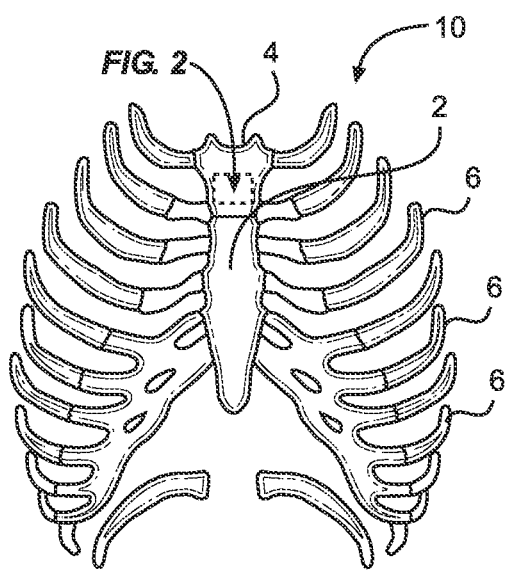
FIG. 1 illustrates a schematic view of a ribcage of a human.
Figure 2:
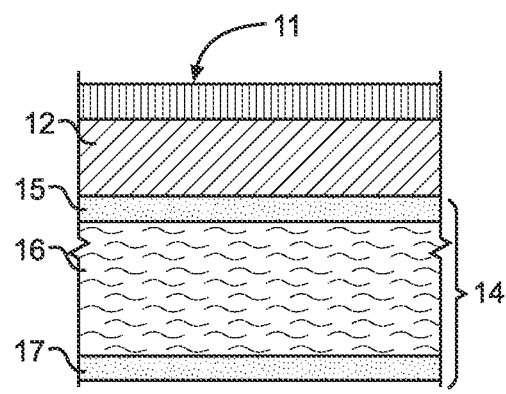
FIG. 2 illustrates a cross-section view of a region of the sternum of a human.

FIG. 1 depicts a schematic view of the ribcage 10 of a human. The sternum 2 is a flat, narrow bone between the ribs 6 comprising three segments: the manubrium, the body, and the xiphoid process. The sternum also comprises a sternal notch 4 (also called the "suprasternal notch" or the "jugular notch"), which is a U-shaped anatomical feature located above the sternum, below the throat, and between the clavicles. FIG. 2 shows a cross-sectional view of a portion of the sternum 2. Skin 11 overlays a layer of subcutaneous tissue 12, which in turn overlays bone 14. Bone 14 includes an intraosseous space 16 bounded by anterior compact bone (i.e., anterior cortex) 15 and posterior compact bone (i.e., posterior cortex) 17. Stated another way, the intraosseous space 16 is the region in the bone between the anterior cortex and the posterior cortex. Bone marrow includes blood, blood forming cells, and connective tissue found in the intraosseous space.

Anterior compact bone 15 and posterior compact bone 17 are each approximately 2.0 millimeters (mm) thick and intraosseous space 16 is approximately 10.0 mm thick in most adult patients. Thus, the total thickness of bone 14 is approximately 14.0 mm. The target zone within the intraosseous space 16 is the center, which is approximately 7.0 mm from the upper surface of anterior compact bone 15 in most adult patients.

The intraosseous space 16 may be accessed by an intraosseous (IO) access device, which may include, but is not limited to, a penetrator assembly comprising a hollow needle, hollow drill bit, bone penetrator, catheter, cannula, trocar, stylet, inner penetrator, outer penetrator, needle or needle set, or other device operable to provide access to an intraosseous space or interior portions of a bone. Such IO access devices may be formed, at least in part, from metal alloys such as 304 stainless steel and other biocompatible materials associated with needles and similar medical devices. A wide variety of IO access devices may be formed in accordance with one or more teachings of the present disclosure. For instance, trocars, spindles, and/or shafts may be disposed within a cannula during insertion at a selected insertion site. Inner penetrators may include such trocars, spindles, and shafts, among others. Further, inner penetrators may comprise various lengths including, but not limited to, 20 to 50 millimeters (e.g., between 35 and 40 mm, 38.5 mm, and/or the like). Outer penetrators may include catheters, cannulas, hollow needles, and hollow drill bits, among others. In some implementations, the penetrator assembly may include a flexible outer penetrator and a rigid inner penetrator as disclosed in international patent application no. PCT/IB2019/053900, which is herein incorporated by reference in its entirety.

Figure 4B:
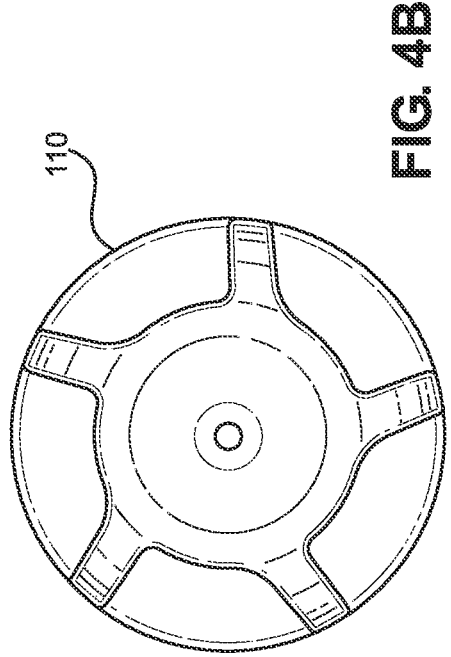
FIG. 4B illustrates a top view of the intraosseous access device of FIG. 4A.
Figure 4C:
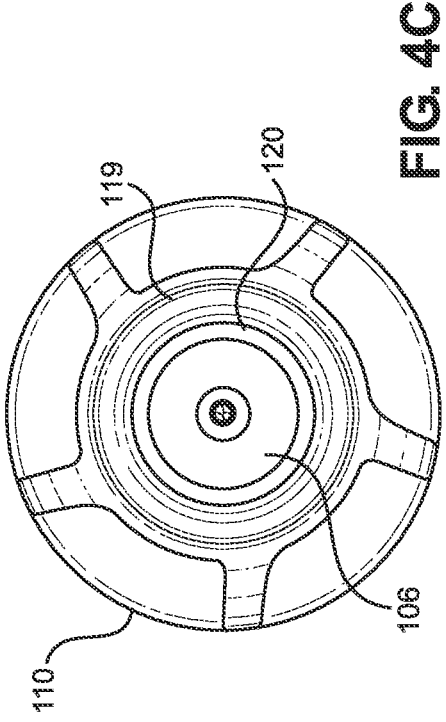
FIG. 4C illustrates a bottom view of the intraosseous access device of FIG. 4A.
Figure 4A:
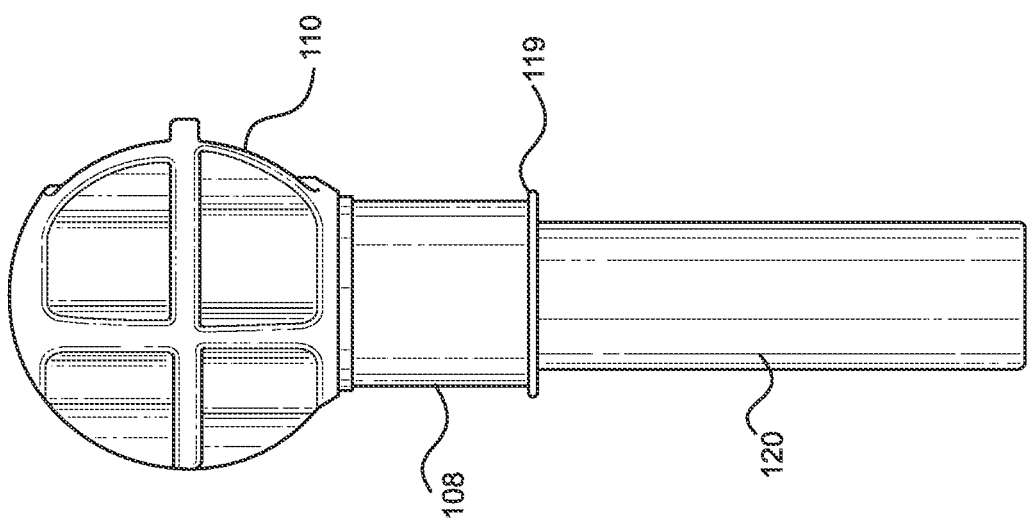
FIG. 4A illustrates a side view of the intraosseous access device of the present disclosure.

FIG. 3 illustrates an implementation of an IO access device 100 of the present disclosure and its components, the IO access device configured for manual insertion into a subject's intraosseous space. The intraosseous access device 100 comprises a manual driver 101 that includes a handle or grip 110 connected to an inner penetrator hub 108, which is attached to a rigid inner penetrator 111. The inner penetrator 111 may, for example, take the form of any suitable stylet or trocar. The inner penetrator 111 includes a distal end having a tip 102 configured to penetrate bone and associated bone marrow. The inner penetrator 111 further includes a proximal end that may have a notch 112 configured to assist in coupling the inner penetrator hub 108 to the inner penetrator 111, as shown in FIGS. 4D and 6. For instance, the inner penetrator hub 108 may be overmolded over the inner penetrator 111 such that the material from the inner penetrator hub may be molded to extend into the notch 112. The inner penetrator hub 108 is surrounded by an annular skirt 105 connected to and extending from the handle 110. A distal end 116 of the skirt 105 includes an annular flange 119 radially extending outwardly therefrom. In some implementations, the inner penetrator 111 extends from the handle or grip 110, and furthermore extends from the distal end 116 of the skirt 105.

The IO access device 100 also includes an outer penetrator hub 106 that is coupled to an outer penetrator 113. The outer penetrator 113 may, for example, take the form of a hollow tube, such as cannula (e.g., a metal cannula), or a hollow drill bit, and which may be configured (e.g., to possess sufficient rigidity) such that the outer penetrator 113 will not buckle or otherwise be damaged as it is inserted through anterior compact bone together with the inner penetrator 111. In other implementations, the outer penetrator 113 may be flexible so that it may be manipulated after insertion into the intraosseous space (i.e., by bending a portion of the outer penetrator to secure it, along with the outer penetrator hub 106, against the patient's skin to provide a lower profile). The outer penetrator hub 106 includes a proximal end 107 and a distal end 109. The outer penetrator 113 also includes a proximal end and a distal end 117, the proximal end of the outer penetrator 113 coupled to the outer penetrator hub 106. The outer penetrator distal end 117 includes a cutting surface operable to penetrate bone and associated marrow. The outer penetrator 113 extends from the distal end 109 of the outer penetrator hub 106.

The inner penetrator hub 108 is configured to removably attach to the outer penetrator hub 106. More particularly, the proximal end 107 of the outer penetrator hub 106 and the inner penetrator hub 108 may be configured as complimentary connectors (with, for example, the inner penetrator hub 108 including a female Luer connector and the proximal end 107 of the outer penetrator hub 106 being configured as a male Luer connector, although these configurations could be reversed in other implementations) to allow the manual driver 101 to be removably coupled to the outer penetrator 113. For example, the outer penetrator hub 106 (and, more specifically, the proximal end 107 of the outer penetrator hub 106) may include an external surface 114 that is threaded and that is proximate a passageway that is in fluid communication with the passageway of outer penetrator 113. The inner penetrator hub 108 may include an internal surface 115 that is threaded to mate with the external threaded surface 114 at the proximal end 107 of the outer penetrator hub 106. The internal threaded surface 115 is proximate to and surrounds a male projection that is tapered to match an inwardly-tapered recess in the proximal end 107 of the outer penetrator hub 106.

The outer penetrator 113 comprises a longitudinal passageway configured to slidably receive a portion of the inner penetrator 111 when the inner penetrator hub 108 is attached to the outer penetrator hub 106, thus forming a penetrator assembly. The handle or grip 110 of the manual driver 101 is configured to manually drive the penetrator assembly into an intraosseous space, such that the handle or grip has an ergonomic shape, such as a round or dome-shaped grip, suitable for grasping and manually applying force during manual insertion of the inner and outer penetrators into the bone and associated bone marrow. The handle or grip 110 is configured to allow manual force to be applied and at the same time permit rotation of the handle during insertion of the penetrator assembly into the TO space.

When the driver 101 and the outer penetrator 113 are coupled to each other, the inner penetrator 111 is disposed within the passageway of the outer penetrator 113, and the inner penetrator tip 102 extends beyond the distal end 117 of the outer penetrator 113. The inner penetrator tip 102 and the outer penetrator distal end 117 are each operable to penetrate bone and associated bone marrow. More particularly, the inner penetrator tip 102 and the outer penetrator distal end 117 are configured to cooperate with each other to form a penetrator assembly tip operable to penetrate bone and associated bone marrow when the inner penetrator hub 108 is attached to the outer penetrator hub 106.

The IO access device 100 may further comprise a protective shield or cover 120, as depicted in FIGS. 4A-4D and 5. The cover 120 is configured to move between a first or extended position operable to provide sharps protection from the distal ends of the inner and outer penetrators, and a second or retracted position operable to guide insertion of the penetrator assembly into an IO space at an insertion site when using a locator, as will be discussed in further detail below. The cover 120 includes a blunt (i.e., not sharp) distal end 121 having an opening 122. The cover 120 further includes a proximal end 124. The cover 120 may have a generally tubular shape and defines a longitudinal bore extending from the distal end 121 to the proximal end 124. The inner penetrator 111 and/or the outer penetrator 113 may be disposed within the opening 122 when the cover is in the first or extended position to protect a user or operator of the IO access device 10 (as well as a subject on which the device will be used) from being inadvertently stuck by the inner and/or outer penetrator tips.

The proximal end 124 of the cover 120 may include a plurality of resilient fingers 125 annularly disposed along its circumference, each finger including a respective ridge or nub 126 protruding radially outward therefrom. The proximal end 124 of the cover 120 may be slidably coupled to the manual driver 101 via a correspondingly shaped internal groove or recess 118 disposed between the inner penetrator hub 108 and the handle 110. For instance, in implementations where the protective shield 120 has a generally tubular shape, the corresponding internal recess 118 is annularly disposed in the driver. More particularly, the respective ridges or nubs 126 disposed on the resilient fingers 125 of the cover 120 are operable to provide a friction fit within the recess 118 of the driver to maintain the cover in a desired position, such as in the extended position or in the retracted position. The cover 120 may be detached from the driver 101, such that the driver can be used for peripheral insertion of the penetrator assembly into an intraosseous space.

In some implementations, the grip 110 and the inner penetrator hub 108 may be attached to each other through a bond created with an ultraviolet (UV) curable adhesive. In other implementations, the grip 110 and the inner penetrator hub 108 may be integral with each other (such as through injection molding), thus forming a single unitary structure. In still other implementations, the grip 110 and the inner penetrator hub 108 may be force coupled, or otherwise adhered to one another, while in other implementations, the grip 110 and the inner penetrator hub 108 may be removably coupled to each other such that they can be separated without destroying, damaging or otherwise impairing the function of either component for re-use. In still other implementations, the grip 110 may be coupled directly to the outer penetrator hub 106 such that there is no intervening inner penetrator hub 108, and with the inner penetrator 111 being attached directly to the grip 110.

The tip 102 of the inner penetrator 111 is pointed and configured to allow the IO access device 100 to be driven into an intraosseous space, such as intraosseous space 16. The inner penetrator 111 fits closely within the passageway of the outer penetrator 113 such that the inner penetrator 111 prevents the outer penetrator 113 from becoming clogged with tissue (e.g., skin, bone, marrow) as the JO access device 100 is driven into an insertion site of a subject (e.g., a patient). The inner penetrator tip 102 and the outer penetrator distal end 117 may be ground together to form corresponding cutting surfaces in some implementations where both the inner penetrator 111 and the outer penetrator 113 comprise a suitable metal. In other implementations, the inner penetrator tip 102 and the outer penetrator distal end 117 may be ground separately to form corresponding cutting surfaces configured to penetrate bone and associated marrow. Once the JO access device 100 is properly positioned at the insertion site, the manual driver 101 can be disengaged from the outer penetrator hub 106 such that the proximal end 107 (which may take the form of a male Luer lock) is exposed and a conduit is formed from the outer penetrator hub 106 through the outer penetrator 113 to the intraosseous space. A fluid source may then be coupled to the proximal end 107 of the outer penetrator hub 106 to deliver fluid through the outer penetrator 113 and into intraosseous space.

FIGS. 7A-7E depict various views of a sternal locator 200 for use with the IO access device 100. The locator 200 is operable to help a user locate an insertion site on the sternum of a patient and facilitate insertion of the IO access device 100 into the intraosseous space. The locator 200 comprises a circumferential collar 210 and a base 230 projecting from the circumferential collar 210. The base 230 comprises a top surface 232 and an underside surface 236. The base 230 also comprises an alignment feature 234, as will be discussed in detail below.

The circumferential collar 210 comprises a collar contact surface 212 and an annular through-hole or passageway 214 extending through the locator. The collar 210 further comprises a plurality of longitudinally-oriented resilient locking tabs 216 that are spaced apart from each other (i.e., circumferentially-spaced apart from each other at 120 degree intervals). In some implementations, there may be three locking tabs 216, as depicted in the figures. In other implementations, there may be more or fewer locking tabs 216 (e.g., 1, 2, 3, 4, 5, 6, 7, 8, or more tabs). The through-hole 214 extends from the collar contact surface 212 to the underside 236 of the base. The collar contact surface 212 is configured to contact the annular flange 119 at the distal end 116 of the skirt 105 to impede further insertion of the penetrator assembly into the intraosseous space, thus providing a depth stop for the IO access device. The collar contact surface 212 is an example of a proximal-facing surface adjacent a passageway configured to receive a penetrator of an IO access device.

The collar 210 is configured to couple the locator 200 to the IO access device 100, and more particularly, the one or more locking tabs 216 of the collar 210 are configured to secure the locator 200 to the IO access device 100. For example, each locking tab 216 has an inwardly-projecting portion 216i that includes a surface 216s that is configured to overlie a portion of the inner penetrator hub 108 (and, more specifically, the flange 119 at the distal end 116 of the skirt 105) of the IO access device 100. At least a portion of each surface 216s may be oriented at a non-zero (e.g., perpendicular) angle relative to the direction of insertion of the IO access device 100. More particularly, each surface 216s may be configured with a shape that complements the shape of a portion of the flange 119 at the distal end 116 of the skirt 105 it will contact after the IO access device 100 is inserted into the intraosseous space, which portion may be on a proximally-facing surface of the flange 119. As a result, the surfaces 216s are configured to resist or impede removal of the inner penetrator 111 after the inner and outer penetrators 111, 113 are inserted into the intraosseous space.

Each locking tab 216 (and, more specifically, each vertical component 216v of each tab 216) is configured to flex outward away from the center of the collar 210 as inwardly-tapered exterior surface 216t of the projecting portion 216i contacts a distally-facing surface of the flange 119 at the distal end 116 of the skirt 105, then snap inward as the surface 216s passes over the flange 119, thus locking the IO access device 100 in place. It should be appreciated that the number of locking tabs used may be adjusted to best suit the shape of the IO access device being used.

The locking tabs 216 are configured to stabilize the IO access device both by resisting any outward longitudinal movement of the IO access device (meaning movement out of the intraosseous space along the direction of insertion) as well as any movement that would otherwise result from the IO access device canting from side-to-side or otherwise moving laterally. The collar 210 also includes longitudinally-oriented elements 256 that have inwardly-tapered surfaces 256t and curved inner surfaces (which are shaped like the inside of a cylinder) 256s. These elements are taller than the locking tabs 216 and function to guide the IO access device to the proper location as it enters the space bounded by the collar 210, which also helps to prevent damage to the tabs 216. The longitudinally oriented elements 256 also help to resist any lateral pitching or movement of the IO device. Each element 256 includes at least one longitudinally-oriented rib 258 that serves to increase the rigidity (and tendency to resist lateral bending) of the element 256. Each rib includes an enlarged portion that surrounds a portion of a bone probe 30.

The alignment feature or notch 234 of the locator 200 is an arc-shaped portion of the base 230. The alignment feature 234 is configured to approximate the shape of sternal notch 4 of a human patient and is operable to indicate proper placement of the locator 200. The locator is properly located on the chest of a patient when it is placed over the sternum such that the sternal notch is visible and at least partially (and, preferably, completely) bounded by alignment feature 234.

The most inwardly-curved portion of the alignment feature 234 is spaced a distance $D_A$ from the center of the through-hole 214 (that is, $D_A$ is the shortest distance between the hole 214 and the alignment feature 234). In some implementations, $D_A$ may be about 21 mm. In other implementations, $D_A$ may range from about 10 mm to about 35 mm. The outer edge of the base 230 may be about 7 mm from the nearest location on the closest locking tab 216, such that a distance $D_F$ may be about 7 mm. In other implementations, $D_F$ may range from about 0 to 15 mm. Some other implementations of the present locators 200 may not include the base 230.

Figure 7A:
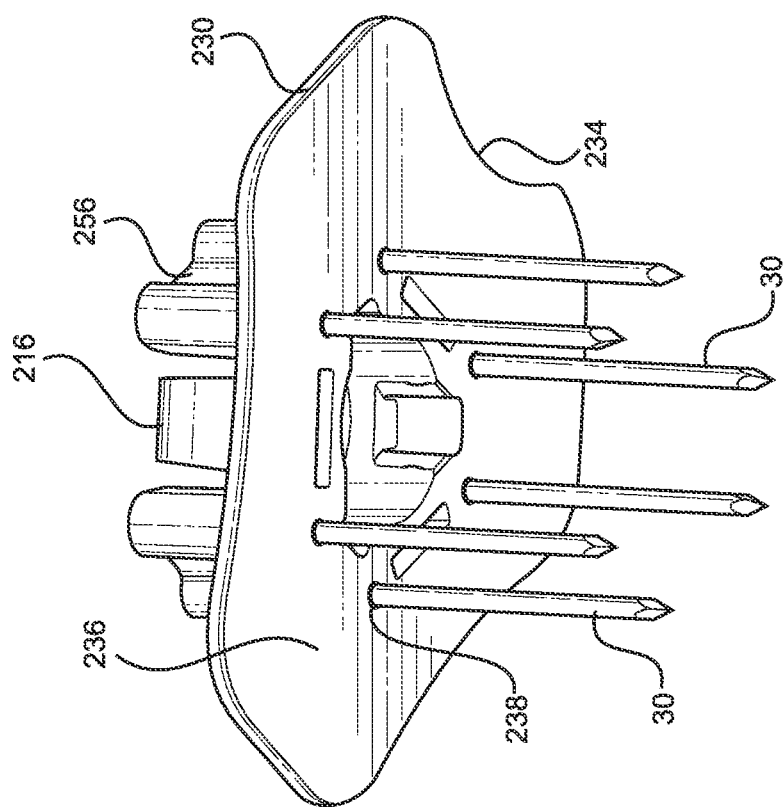
FIG. 7A illustrates a top perspective view of a sternal locator of the intraosseous access device of the present disclosure.
Figure 7B:
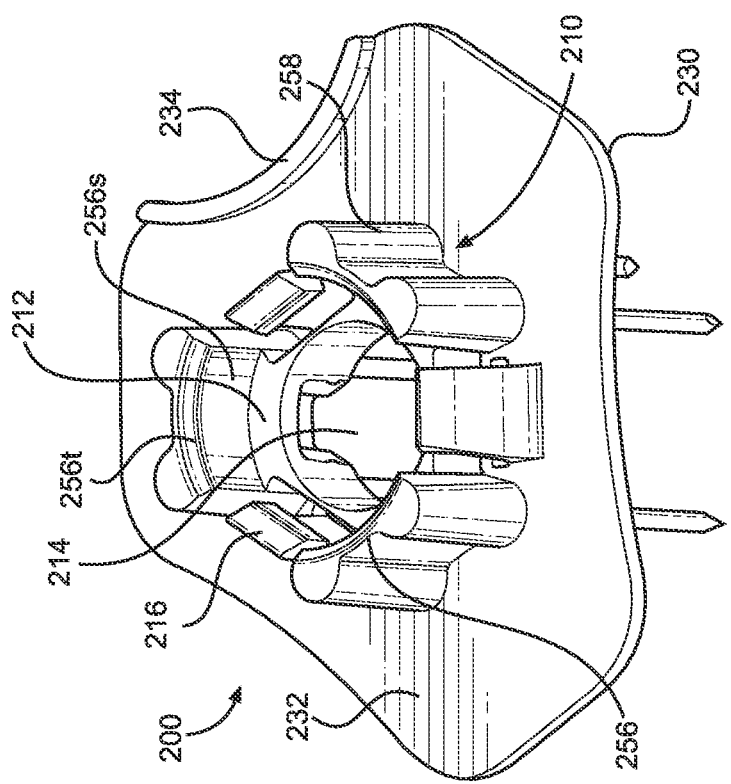
FIG. 7B illustrates a bottom perspective view of the sternal locator of the present disclosure.
Figure 7D:
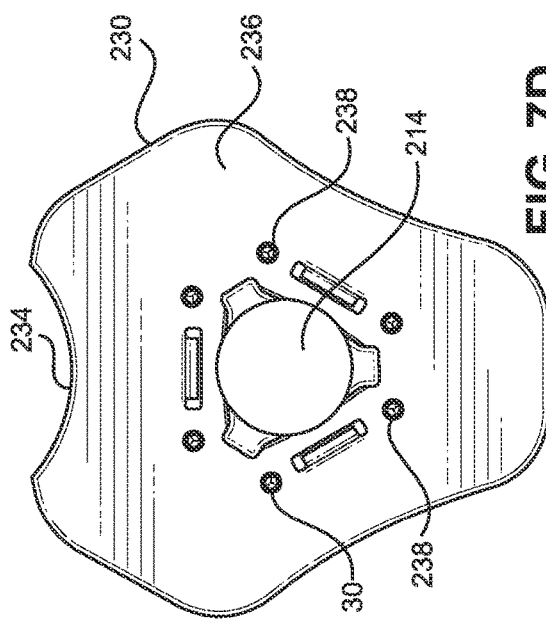
FIG. 7D illustrates a bottom view of the sternal locator of the present disclosure.
Figure 7E:
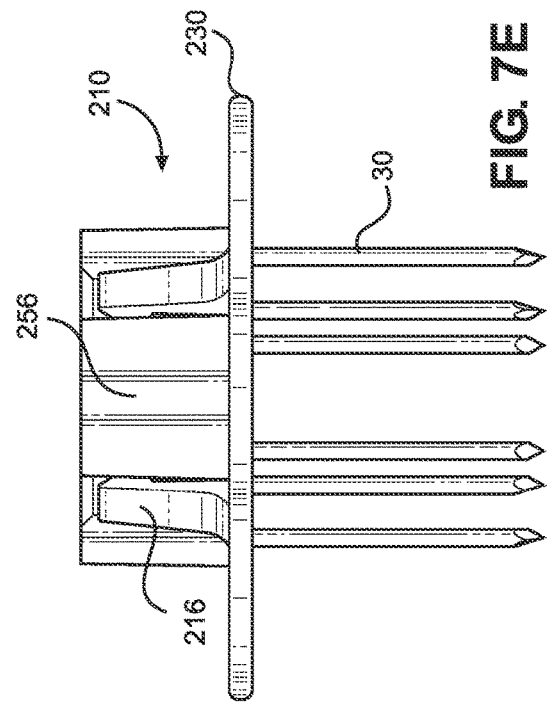
FIG. 7E illustrates a side view of the sternal locator of the present disclosure.
Figure 7C:
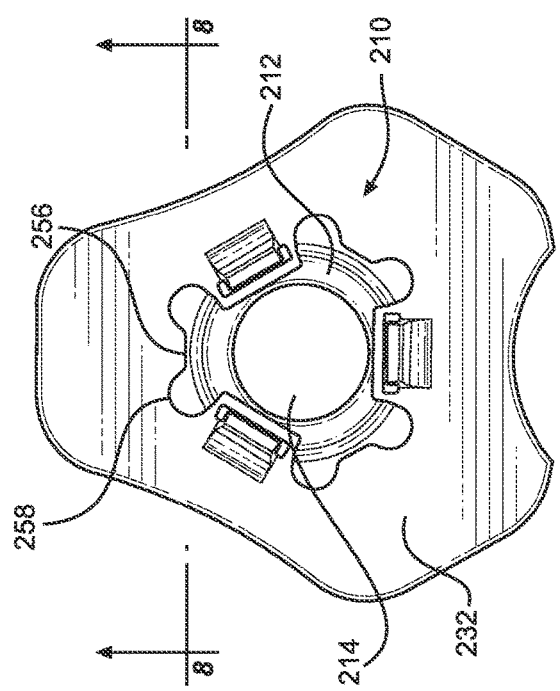
FIG. 7C illustrates a top view of the sternal locator of the present disclosure.
Figure 8:
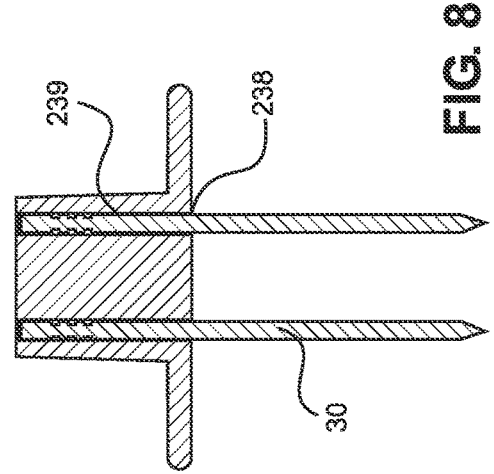
FIG. 8 illustrates a cross-sectional view of the sternal locator shown along line 8-8 in FIG. 7C.

The locator 200 comprises a plurality of openings 238 in the underside 236 of the base 230. For instance, FIGS. 7B and 7D depict six openings 238, although other implementations may have more or less openings (e.g., 1, 2, 3, 4, 5, 6, 7, 8, or more openings). A recess 239 extends from each opening 238 into a respective rib 258 of a corresponding longitudinally-oriented element 256. Each recess 239 is configured to receive a respective bone probe 30, as shown in FIG. 8. Other implementations may comprise more or fewer recesses (and associated openings) configured to respectively receive more or fewer bone probes 30.

Figure 9A:
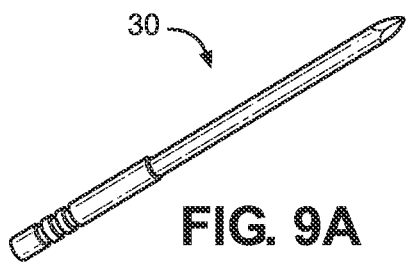
FIG. 9A illustrates a perspective view of a bone probe in accordance with the present disclosure.
Figure 9B:
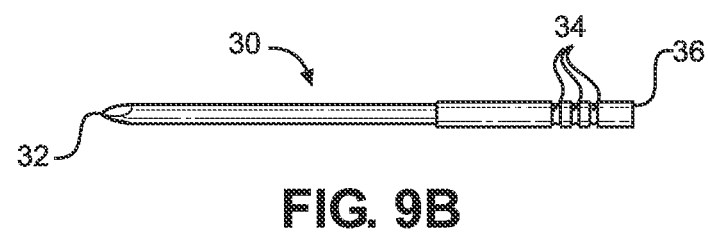
FIG. 9B illustrates a side view of the bone probe of FIG. 9A.

As shown in FIGS. 9A and 9B, each probe 30 comprises a pointed tip 32, a plurality of circumferential grooves or notches 34, and a proximal end 36, where the notches 34 are closer to the proximal end 36 than to the tip 32. The probes 30 may comprise stainless steel, though other suitable sterile or biocompatible materials (or materials capable of being made sterile before use on a patient) may be used. The proximal end 36 is configured to be inserted into the opening 238 and corresponding recess 239 of the locator 200. In some implementations, the bone probes 30 may be fixed to the locator 200, such as by being bonded to the locator 200 using UV-curable adhesive applied to the recess 239 and/or the grooves 34 and/or the proximal end 36 of the probe 30. In other implementations, the bone probe 30 may be force fit through the opening 238 and into the recess 239 such that it is held in place by friction between the probe and the surface of the locator against which it is in contact with, thus forming an interference fit. In still other implementations, the probes 30 may be fixed to the locator 200 as part of an injection molding process or using epoxy. Each probe 30 may comprise any of various lengths and can extend, for example, approximately 19-24 millimeters from a proximal-facing surface adjacent a passageway (e.g., from the collar contact surface 212).

Figure 9C:
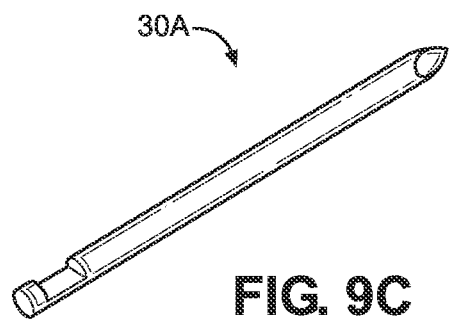
FIG. 9C illustrates a perspective view of another implementation of a bone probe in accordance with the present disclosure.
Figure 9D:
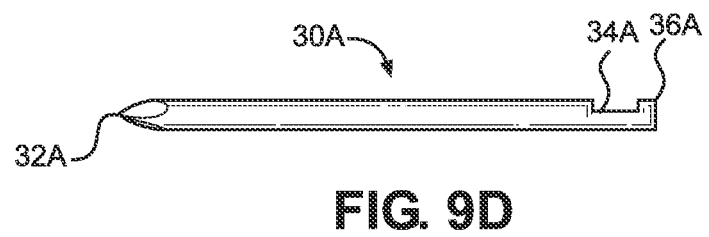
FIG. 9D illustrates a side view of the bone probe of FIG. 9C.

FIGS. 9C and 9D depict another implementation of bone probes 30a that are suitable for use with the locator 200. Each probe 30a comprises a pointed tip 32a, a groove or notch 34a, and a proximal end 36a, where notch 34a is closer to the proximal end 36a than to the tip 32a. Each probe 30a may comprise stainless steel, though other suitable sterile or biocompatible materials (or materials capable of being made sterile before use on a patient) may be used. The proximal end 36a is configured to be inserted through the opening 238 and into the corresponding recess 239 of the locator 200. Probes 30a may be fixed to the locator 200, such as by being bonded to locator 200 using UV-curable adhesive applied to the recess 239 and/or the notch 34a and/or the proximal end 36a of the probe 30a. In other implementations, the probe 30a may be force fit in the opening 238 and the recess 239 such that it is held in place by friction between the probe and the surface of the locator against which it is in contact, thus forming an interference fit. In other implementations, the probes 30a may be fixed to the locator 200 as part of an injection molding process or using epoxy. The probe 30a may comprise any of various lengths and can extend, for example, approximately 19-24 millimeters from a proximal-facing surface adjacent a passageway (e.g., from the collar contact surface 212).

Figure 10A:
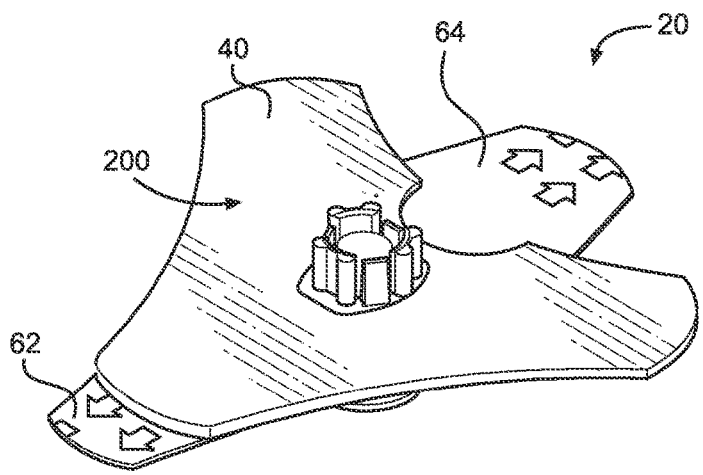
FIG. 10A illustrates a perspective view of a stabilizer in accordance with the present disclosure.

FIG. 10a illustrates a stabilizer 20 configured to be placed on the chest of a subject (e.g., a human patient) at a location near the sternum 14 and aligned with the sternal notch 4. The stabilizer 20 is also configured to ensure proper placement of an IO access device in the intraosseous space 16. The stabilizer 20 comprises the locator 200, the base of which is located between and coupled to a stabilizer dressing including a top sheet 40 and an adhesive patch 50. Further, the top sheet 40 and the adhesive patch 50 are coupled to each other. The adhesive patch 50 comprises an adhesive configured to adhere the stabilizer 20 to a subject during use (e.g., to the skin on the chest of a human patient).

The top sheet 40 may comprise single-sided tape, such as 3M 1526 polyethylene single coated tape. The top sheet 40 may be oriented such that the adhesive side of the tape couples top sheet 40 to the top surface 232 of the base 230 and to adhesive patch 50. The adhesive patch 50 may comprise any standard medical grade adhesive. For example, the adhesive member may comprises double-sided tape, such as 3M 1522 transparent polyethylene double coated tape. One side of the adhesive patch 50 is coupled both to underside 236 of base 230 and to top sheet 40, while the other side of adhesive patch 50 is coupled to at least one liner (e.g., a release liner).

Figure 10B:
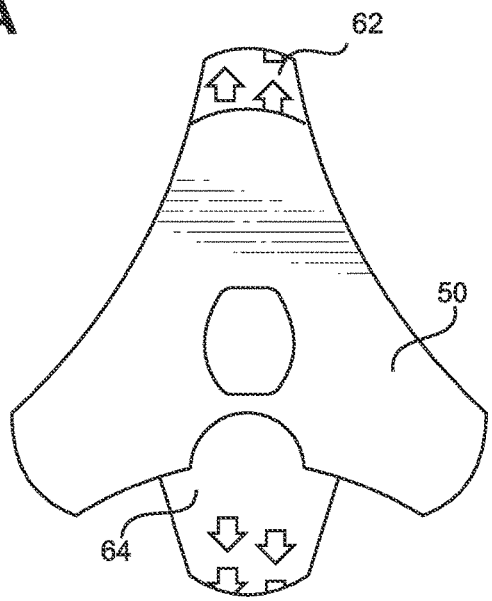
FIG. 10B illustrates a top view of an adhesive patch of the stabilizer in accordance with the present disclosure.
Figure 10C:
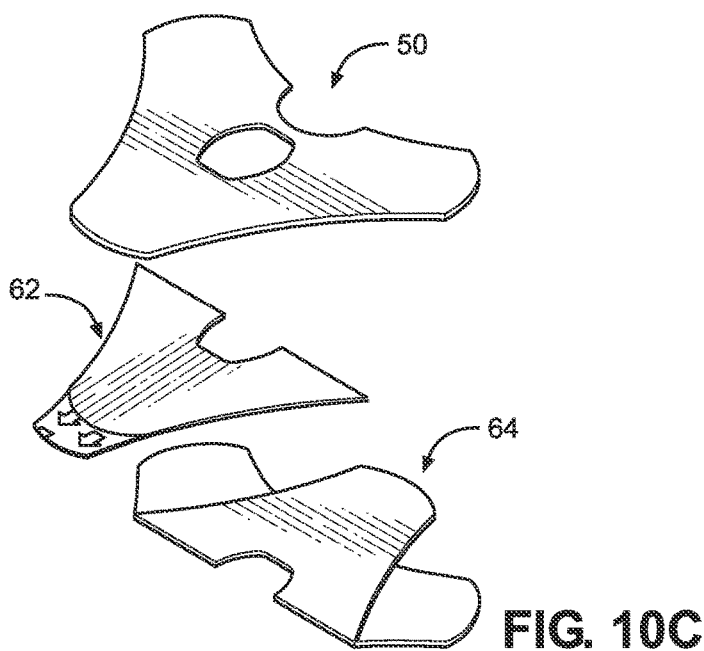
FIG. 10C illustrates a perspective view of the adhesive patch in accordance with the present disclosure.

As shown in FIGS. 10b and 10c, the adhesive patch 50 is coupled to a removable first liner 62 and a removable second liner 64. The removable liners 62, 64 cover the bottom adhesive side of the adhesive patch 50 (e.g., to prevent the stabilizer 20 from undesired sticking). When the stabilizer 20 is ready to be used, the liners 62, 64 can be removed by a user and the stabilizer 20 can be placed on the chest of a patient.

Some implementations of the stabilizer may not include top sheet 40 or adhesive patch 50. For example, the stabilizer 20 may lack any adhesive features for coupling the template to the chest of a patient. In still other implementations, the underside 236 of the base 230 may be coated with an adhesive directly applied to the locator 200 (that is, without requiring a tape layer as discussed above). In such implementations, one or more liners may be coupled directly to the locator 200 to prevent undesired sticking. Implementations of the stabilizer that include an adhesive, such as one applied directly to the underside of the flange of the stabilizer or one on the bottom (distal) surface of an adhesive member, may be configured to adhere to skin on a subject patient.

Figure 11:
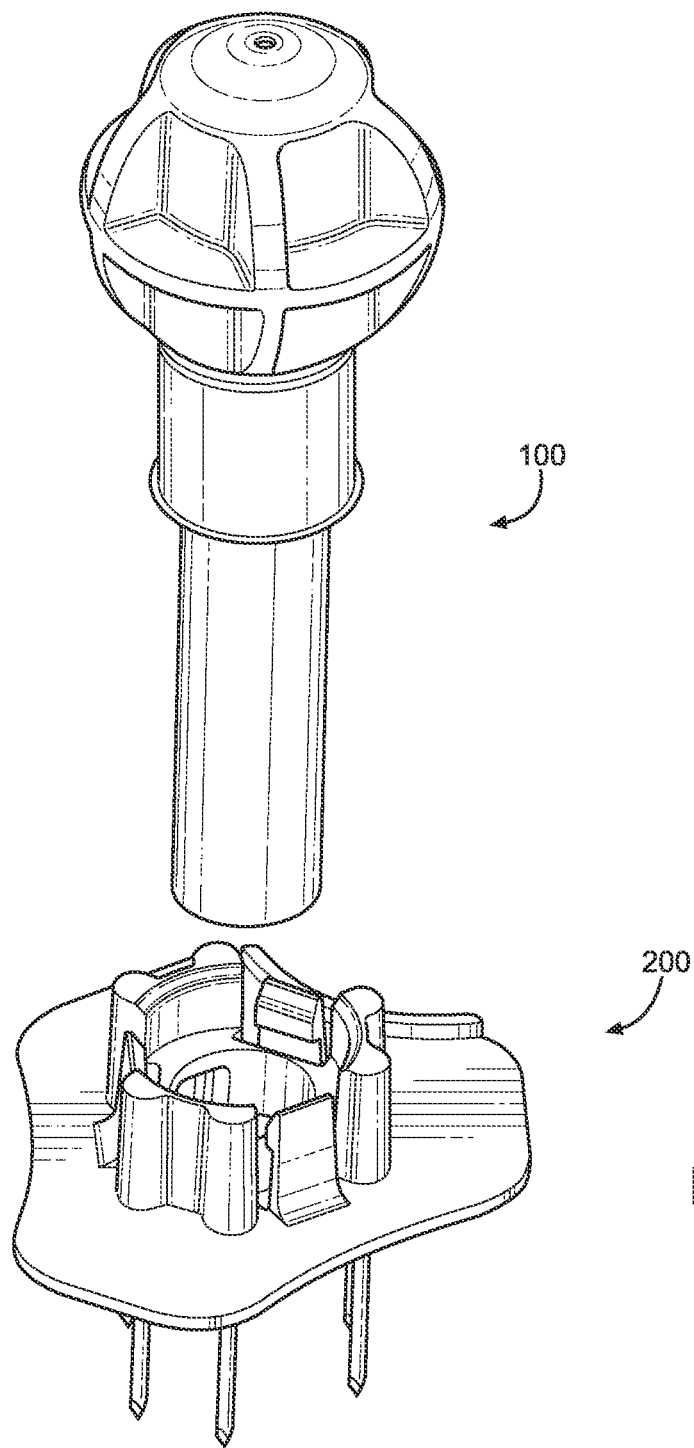
FIG. 11 illustrates a perspective view of an intraosseous access device and locator assembly in accordance with the present disclosure.

FIG. 11 depicts an intraosseous access assembly comprising the IO access device 100 and the locator 200 prior to use on a patient (top layer 40 and adhesive patch 50 have been omitted for clarity). The locator 200 is operable to locate a preferred location for the IO access device 100 to be inserted (e.g., driven) into the sternum of a patient, i.e., by using the alignment feature 234 as previously described in detail above. The locator 200 is further configured to guide insertion of the IO access device 100 into the intraosseous space, i.e., by using the cover 120 as a guide for passing the penetrator assembly of the IO access device through the through-hole 214 of the locator and into the intraosseous space of the patient. Prior to use on a patient, the cover 120 is operable to provide sharps protection from the distal ends of the inner and outer penetrators. The cover 120 is also operable to provide sharps protection from the distal end of the inner penetrator when the driver is decoupled from the outer penetrator after accessing the intraosseous space.

FIGS. 12 and 13 depict the intraosseous access assembly comprising the IO access device 100 coupled to the locator 200 while in use on a human patient (top layer 40 and adhesive patch 50 have been omitted for clarity). $D_1$ is the distance from the collar contact surface 212 to the top surface 232 of the base 230. $D_2$ includes the thickness of the base 230 and any adhesive on the underside 236 or any adhesive patch 50 (not shown). $D_3$ is the distance from the underside 236 or any adhesive or adhesive member attached to the underside 236 to the tip 32 of the bone probe 30. $D_4$ is the distance from bone probe tip 302 to the tip 102 of the inner penetrator 111. Therefore, the overall exposed length of the penetrator assembly (the portion of the inner and outer penetrators 111, 113 that extends beyond the outer penetrator hub 106) is $D_1+D_2+D_3+D_4$.

In some implementations, $D_1$ may be about 5.25 mm, $D_2$ may be about 2.0 mm, $D_3$ may be about 23.5 mm, and $D_4$ may be about 7.75 mm; and therefore, about 38.5 mm of the penetrator assembly may be exposed or protrude beyond the outer penetrator hub 106. Further, the bone probes 30 may be exposed or protrude beyond the underside 236 of the locator 200 by about 23.5 mm. In some implementations, the inner penetrator 111 may protrude about 1.5 mm beyond the outer penetrator 113. When the IO access device 100 is coupled to the locator 200 such that the tabs 216 are in a locked position (and the surfaces 216s bear against the upper surface of the flanged portion 119 of the distal end 116 of the skirt 105), the inner penetrator 111 may extend about 7.0 to 8.0 mm beyond each of the plurality of bone probes 30. Depending on the application, the exposed portions of inner and outer penetrators 111, 113 and the bone probes 30 may be lesser or greater than what is shown and described. For instance, the inner penetrator 111 and the bone probes 30 may be shorter when the sternal locator 200 and the IO access device 100 are intended for use on infants or children (and the inner penetrator 111 may extend a shorter distance beyond probes 30). Further, the inner penetrator 111 and the probes 30 may be longer (and inner penetrator 111 may extend a greater distance beyond probes 30) when the sternal locator and IO access device are intended for use on obese patients, large patients, or patients with a thicker than normal sternum. In other implementations, $D_1$ may be about 5.25 mm, $D_2$ may be about 1.25 mm, $D_3$ may be about 23.5 mm, and $D_4$ may be about 6.0 mm; such that about 32 mm of the penetrator assembly may be exposed or protrude beyond the outer penetrator hub 106 and/or about 19.5 mm of probes 30 protrudes beyond the underside 236 of the locator 200. Any dimension listed herein as "about" may also be substantially (including exactly) equal to the given value.

To use the sternal locator 200, a user first locates the sternal notch 4 of a patient by feeling for the U-shaped cavity above the sternum, below the throat, and between the clavicles. The user then aligns the alignment feature 234 of the locator with the sternal notch 4, ensuring that the balance of the sternal locator is positioned over the patient's sternum. With the sternal locator 200 thus properly aligned, the user then applies pressure to the sternal locator 10, such that the bone probes 30 penetrate skin 11 and muscle 12, until the bone probes touch the anterior compact bone 15 (the top surface of the sternum). Thus, the bone probes 30 provide a depth stop for the locator 200 once they contact bone. The bone probes 30 may penetrate into the anterior compact bone 15 by some marginal distance, such as about 0.5 mm to about 1.0 mm, but do not penetrate into the intraosseous space 16. The user then removes the removable liners 62, 64 of the stabilizer dressing and presses the adhesive patch 50 against skin 11, thus ensuring that adhesive patch 50 is adhered to the skin of the patient.

The thickness of skin 11 and subcutaneous tissue 12 may be equal in thickness to $D_3$, the exposed length of the bone probes 30. However, the thickness of skin 11 and subcutaneous tissue 12 can vary widely depending on the patient. Thus, in some patients, the length of the probes 30 may exceed the tissue thickness such that the locator base 230 is not flush with the skin 11, and portions of the probes 30 are therefore exposed. In such instances, the adhesive layer 50 provides an additional stabilizing effect by affixing the sternal locator 200 to the patient's chest.

Once the stabilizer 200 has been securely affixed to the patient's chest, the user then introduces the distal portion of the IO access device 100 (which includes the inner penetrator tip 102, the outer penetrator distal end 117, and the distal end of the cover 120) into the through-hole 214 in the base 230 of the locator 200. The through-hole 214 includes a complimentary annular shape to that of the tubular cover 230 so that the cover is guided through the through-hole when inserted. The user applies pressure and rotates, twists or reciprocates IO device 100 (which may be back and forth, but not necessarily all the way around, such that the driving movement may be characterized as reciprocating, twisting, or non-rotational (meaning one complete revolution is not utilized)) until the inner penetrator 111 and the outer penetrator 113 pierce the skin 11, the subcutaneous tissue 12, and the anterior compact bone 15. During this insertion procedure, the distal end 121 of the cover 120 contacts the skin 11 without penetrating it since the distal end is blunt (i.e., not sharp). The cover 120 then moves from the extended position to the retracted position as the inner and outer penetrators are inserted into the intraosseous space. In some instances, the intraosseous access device 100 may be used without the locator 200 at peripheral insertion site, such as a patient's humerus or tibia. During such a peripheral insertion procedure, the distal end 121 of the cover 120 contacts the skin 11 without penetrating it since the distal end is blunt (i.e., not sharp). The cover 120 is operable to move from the extended position to the retracted position as the inner and outer penetrators are inserted into the intraosseous space.

As previously described, the collar 210 is, and more specifically the one or more resilient locking tabs 216 of the collar 210 are, configured to couple (e.g., secure) the locator 200 to the IO access device 100. The IO access device 100 is properly positioned when the surfaces 216s of the locking tabs 216 fully engage (or are in contact with) the flange 119 of the distal end 116 of the skirt 105. The rigidity of the resilient locking tabs 216 serves to stabilize the IO access device to which the sternal locator is coupled, both by resisting any outward longitudinal movement of the IO access device (i.e., movement out of the intraosseous space along the direction of insertion) as well as any movement that would otherwise result from the IO access device canting from side-to-side or otherwise moving laterally. The collar 210 also includes longitudinally-oriented elements 256 that are taller than the tabs 216 and which are operable to guide the IO access device to the proper location as the flange 119 of the distal end 116 of the inner penetrator hub enters the space bounded by collar 210, which also helps to prevent damage to tabs 216, and further helps to resist any lateral pitching or movement of the IO access device during an insertion procedure. Each element 256 includes a pair of longitudinally-oriented ribs 258 on opposing sides of the element that serve to increase the rigidity (and tendency to resist lateral bending) of the element 256. Each rib 258 is hollow to receive and surround a portion of a respective bone probe 30.

In some aspects, an audible sound (e.g., a click) may be heard as the tabs 216 pass over the flanged portion 119 of the distal end 116 of the skirt 105 and snap into place. Furthermore, the user may feel the IO access device passing the tabs 216 because the force required to advance the device will be reduced (thus, the user will feel a tactile response of the IO access device "snap" into place). Introducing the IO access device 100 into the patient in this manner may be described as non-surgically introducing (or inserting) the IO access device, or introducing (or inserting) the IO access device without first making an initial incision for the IO access device with a different cutting tool (such as a scalpel). The force that is required to drive the IO access device into locking engagement with the locator may be greater than the force be required to drive the stabilizer through the skin and subcutaneous tissue and into contact with anterior compact bone in most patients.

Figure 14:
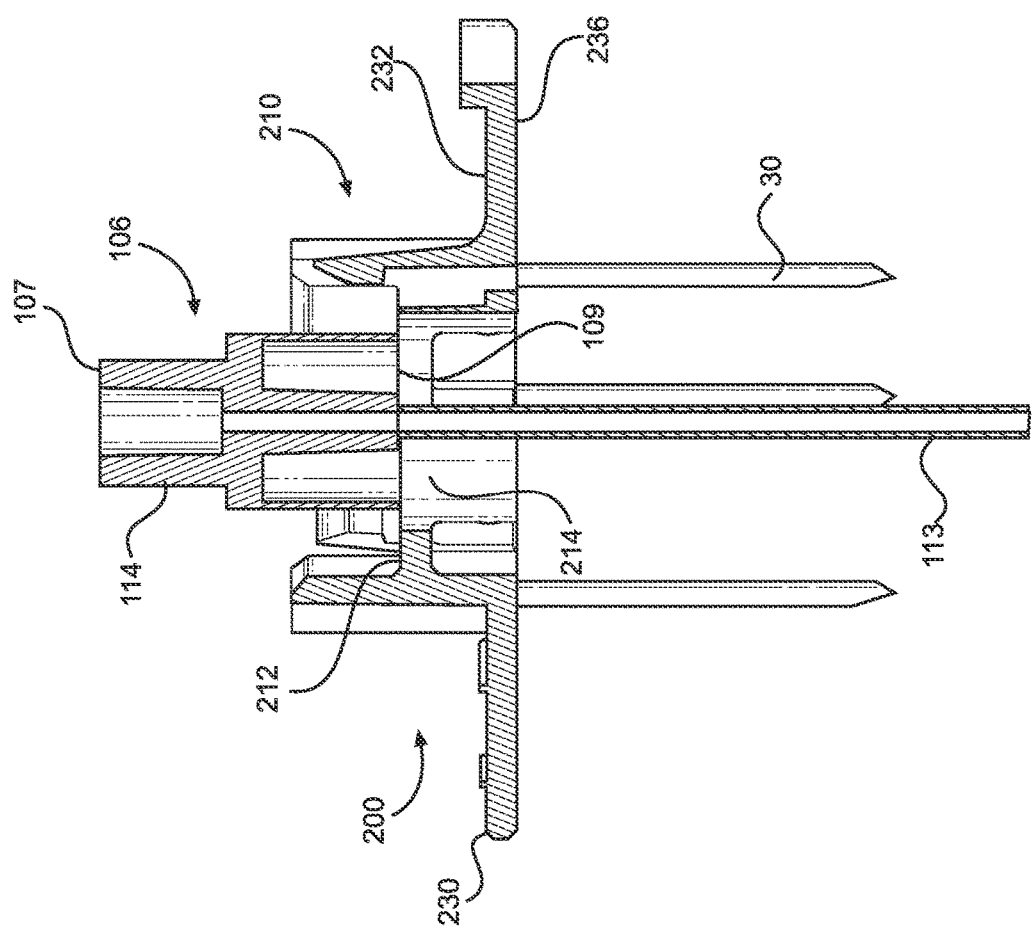
FIG. 14 illustrates a cross-section view of the intraosseous access device and locator assembly with the manual driver removed in accordance with the present disclosure.

As shown in FIG. 14, the driver 101 (including the grip 110, the inner penetrator hub 108 and associated inner penetrator 111, and the cover 120) may then be removed from the outer penetrator hub 106. For instance, the inner penetrator hub 108 may be decoupled from the outer penetrator hub 106 by rotating the grip 101 in a counterclockwise direction to disengage the threaded surfaces 114, 115 of the respective outer and inner penetrators. This allows the user to withdraw the inner penetrator 111 from the outer penetrator 113 while the outer penetrator remains disposed within the intraosseous space. A conduit is thus formed from the open proximal end 107 of the outer penetrator hub 106 through an opening at the outer penetrator distal end 117, which is in direct fluid communication with intraosseous space 16. In some implementations, a flexible outer penetrator may be utilized so that it may be manipulated and secured to the patient after the stabilizer assembly is removed in order to provide a lower profile (i.e., by bending the outer penetrator down to secure it against the skin).

A fluid source may then be coupled to the proximal end 107 of the outer penetrator hub 106 for delivery of fluid (e.g., blood or medicine) to intraosseous space 16 or aspiration of fluid from the intraosseous space. Further, upon removal of the driver 101 from the outer penetrator hub 106 and the locator 200, the cover 120 is operable to move back to the extended position from the retracted position to provide sharps protection from the distal tip 102 of the inner penetrator 111.

The sternal locator 200 is also configured to be withdrawn from the patient's chest while the outer penetrator 113 remains disposed within the intraosseous space. In particular, as the locator is withdrawn from the patient, the through-hole 214 passes over the outer penetrator hub 106 without dislodging the outer penetrator 113 from the intraosseous space. The diameter of the through-hole 214 of the locator 200 is larger than the diameter of the outer penetrator hub 106, such that the locator can be freely lifted over the hub without bumping into it. After the locator has been withdrawn from the patient, the bone probes 30 may be inserted into penetrable material of a sharps container.

A kit may be provided that includes a package (e.g., a flexible package, such as one that does not include a rigid plastic tray) comprising at least one of the present sternal locators, one of the present stabilizers, one of the present sharps containers, and, one of the disclosed IO access devices, as well as instructions for use, which instructions may be provided on the outside of the package, on one of the aforementioned components, and/or on an insert contained within the package. Further, non-limiting examples of suitable materials for the present locators, grips, and hubs described above may include injection moldable plastics, such as polycarbonate. A non-limiting example of a suitable material for the present inner penetrator, outer penetrator, and probes described above may include stainless steel, such as 304V stainless steel.

While the intraosseous access device and locator assembly has been described in terms of what may be considered to be specific aspects, the present disclosure is not limited to the disclosed aspects. Moreover, the many features and advantages of the disclosure are apparent from the detailed specification, and thus, it is intended by the appended claims to cover all such features and advantages of the disclosure which fall within the spirit and scope of the disclosure. Further, it is not desired to limit the disclosure to the exact construction and operation illustrated and described, and accordingly, all suitable modifications and equivalents may be resorted to, falling within the scope of the disclosure. Accordingly, the present disclosure should be considered as illustrative and not restrictive. As such, this disclosure is intended to cover various modifications and similar arrangements included within the spirit and scope of the claims, which should be accorded their broadest interpretation so as to encompass all such modifications and similar structures.

What is claimed is:

1. An apparatus for accessing an intraosseous space within a bone of a patient, the apparatus comprising:
    a penetrator assembly having a sharp penetrating end configured to penetrate the bone and associated bone marrow;
    a manual driver coupled to the penetrator assembly, the manual driver including a handle operable to manually drive the penetrator assembly into the bone and associated bone marrow; and
    a protective shield having a distal end and a proximal end, the protective shield slidably coupled to the handle and defining a longitudinal hollow passageway extending between the distal end and the proximal end;
    where the protective shield is operable to move between an extended position in which the sharp penetrating end of the penetrator assembly is disposed within the longitudinal hollow passageway of the protective shield to provide sharps protection, and a retracted position in which the sharp penetrating end of the penetrator assembly is disposed outside the longitudinal hollow passageway of the protective shield to permit penetration of the penetrator assembly into the intraosseous space; wherein the penetrator assembly further comprises an outer penetrator defining a longitudinal hollow bore, and an inner penetrator slidably receivable within the hollow bore of the outer penetrator.

2. The apparatus according to claim 1, wherein the distal end of the protective shield defines an opening sized to receive the penetrator assembly.

3. The apparatus according to claim 2, wherein the distal end of the protective shield includes a blunt surface operable to contact a patient's skin without cutting the skin.

4. The apparatus according to claim 2, wherein the protective shield is removably coupled to the handle.

5. The apparatus according to claim 2, wherein the driver further comprises an internal recess configured to slidably receive the protective shield.

6. The apparatus according to claim 5, wherein the proximal end of the protective shield includes a resilient finger.

7. The apparatus according to claim 6, further comprising at least two spaced-apart resilient fingers disposed along a circumference of the proximal end of the protective shield.

8. The apparatus according to claim 7, wherein each resilient finger includes an outwardly protruding ridge configured to provide a friction fit within the internal recess of the driver to maintain the protective shield in a desired position.

9. The apparatus according to claim 5, wherein the internal recess has a shape corresponding to a shape of the protective shield.

10. The apparatus according to claim 9, wherein the protective shield is generally cylindrical, and the internal recess is correspondingly annular.

11. The apparatus according to claim 1, wherein the inner penetrator comprises a rigid stylet, and the outer penetrator comprises a flexible cannula.

* * * * *